United States Patent [19]

Bolanowski

[11] 4,121,711
[45] Oct. 24, 1978

[54] PACKAGE FOR A MULTIPLE OF STERILE SURGICAL SUTURES WITH OR WITHOUT NEEDLES ATTACHED

[75] Inventor: Lelia Bolanowski, Bethel, Conn.

[73] Assignee: American Cyanamid Company, Stamford, Conn.

[21] Appl. No.: 799,640

[22] Filed: May 23, 1977

[51] Int. Cl.² .................. A61L 17/02; B65D 85/24
[52] U.S. Cl. .................. 206/63.3; 206/382
[58] Field of Search .................. 206/63.3, 380, 382, 206/383, 329, 485

[56] References Cited

U.S. PATENT DOCUMENTS

| 203,958 | 5/1878 | Thomas | 206/38 D |
|---|---|---|---|
| 2,426,899 | 9/1947 | Pantalone | 206/329 |
| 2,692,676 | 10/1954 | Grover | 206/63.3 |
| 2,839,188 | 6/1958 | Cipriani et al. | 206/329 |
| 3,202,273 | 8/1965 | Riall | 206/63.3 |
| 4,014,434 | 3/1977 | Thyen | 206/63.3 |

Primary Examiner—William T. Dixson, Jr.
Attorney, Agent, or Firm—Charles F. Costello, Jr.

[57] ABSTRACT

The package consists of a card which holds the sutures. The sutures are loaded onto the card by holding them on needle retention slits or placing them on a layer of foam and then passing them through suture loading openings into suture retaining holes. When the sutures are longer than the card, the suture loop is held by suture retention slits through doublebackstringing.

The card is enclosed in a suture sleeve comprising two needle side flaps and a needle protection flap. When the flaps are opened and the protection flap is lifted, the needle ends of the loaded sutures are exposed.

A suture package comprising a strippable outer pouch is also described.

8 Claims, 8 Drawing Figures

PACKAGE FOR A MULTIPLE OF STERILE SURGICAL SUTURES WITH OR WITHOUT NEEDLES ATTACHED

BACKGROUND OF THE INVENTION

This invention relates to a suture package which permits dispensing of the suture from a self-contained paperboard sleeve containing a paper card or from the paper card itself after the card is removed from the sleeve. This invention also relates to a process for inserting the suture into the paper card.

A suture is a strand of material, with or without an attached needle or needles, using for suturing, ligating or other surgical procedures.

The packaging of many commercial products is essential to the proper end use of the product and thus forms an integral part of the overall product design. The significance of packaging is most evident in the packaging of surgical sutures. It is essential that the package protect the product and maintain sterility throughout its period of potential use. Sutures may be stored in hospitals for several years, although the usual storage time is much shorter. It is essential that the package provide rapid and positive means of identification and release the product undamaged ready for use by the surgeon. There are many sizes of sutures, and many materials of construction such as catgut or polyglycolic acid for absorbables, silk, cotton, nylon, dacron, polyethylene, polypropylene, stainless steel, insulated stainless steel and other materials for use as nonabsorbables. There are several different needle types in common use including pointed straight, pointed curved, three cornered straight, three cornered curved, curved both regular and reverse cutting, and needles with side cutting edges of various types. The variations and combinations of each of these to meet the preference of many surgeons for different operative procedures means that the suture manufacturer needs to supply different suture combinations running into the thousands. The importance of positive identification and efficient, economical packaging can thus be readily appreciated.

It is also important to provide convenience to the user and limit the risk of accidently enclosing foreign items in the patient by limiting the number of extraneous packaging materials associated with use of the product in the operating theater. A count is often kept to ensure that each item is accounted for and removed from the operating field. Considering the ramifications of enclosing such material in the patient accidently during surgical procedures, it is obviously essential to minimize this hazard.

It is essential that a suture package containing a surgical needle or needles, protect the suture from contact with the sharp point or cutting edge of the needle which could partially cut the suture or the package. Also, the armed needle edges and point need to be protected so as to maintain their sharpness. Finally, in a package for a multiple of sutures, it is desirable to allow for dispensing of one or more sutures at a time without becoming snarled.

In specific types of surgery, for example, cardiovascular surgery, relatively long sutures are required. Also a lot of sutures of the same needle, size, and material are generally required. Finally, double-armed sutures, i.e., sutures with a needle attached to both ends, as well as single-armed sutures are commonly used in cardio-vascular surgery.

These requirements are so rigorous and of such importance that many different package designs have been tried. For example, see U.S. Pat. Nos. 3,985,277; 3,779,375; 2,692,676 and 2,617,523. These patents are incorporated herein by reference. Generally, these patents disclose a surgical suture or sutures packaged in a plastic or foil strippable outer envelope. Contained in the strippable envelope is a one piece inner envelope. The suture strands are placed lengthwise to the inner envelope. The suture is normally prepared for the surgeon by stripping the outer envelope and transferring the inner envelope by forceps or by projecting into the sterile operating field. The one piece inner envelope is opened at the time of use.

The suture package of the present invention has advantages over these prior art patents. The sutures are contained on a paper card. The card is contained in a sterile paperboard sleeve. The paper card can then be removed from the sleeve with the sutures contained on the card. This has the advantage of allowing positive visual identification of the suture being used. This is important in cardio-vascular surgery where different sizes and types of sutures may be used. Also, the paperboard sleeve is discarded prior to entry into the surgical area. This reduces the amount of material in the operating area. Finally, because the card is removed from the sleeve, the card can be laid flat under a towel on a surgical tray which can then be stacked with instruments for use.

Alternatively, the sleeve containing the card can be laid flat under a towel on a surgical tray. The inside of the needle protection flap of the sleeve can then be labelled allowing positive visual identification of the suture being used.

Another advantage is that more than one card may then be removed and used in tandem. This should facilitate faster and easier dispensing of the sutures.

Another advantage is that because the sutures are contained on the card by holes there is less fraying when the package is transported and during dispensing. This feature is especially important in bioabsorbable sutures, e.g., polyglycolic acid, where the suture is manufactured to dissolve in a certain period of time Still, another advantage is that the dispensibility of the card is not lost when the card is folded. That is, when the suture is placed on the card by use of the holes, the card can then be folded accordion style. The card containing the sutures can then be extended at the point of use and the sutures dispensed from under a sterile towel. Thus, the paper sleeve containing the card can be varied in length. This could be utilized as an identification means for sutures of various sizes or thicknesses.

The suture retention slits are oriented within the card and paperboard sleeve to allow immediate use when grasped by the needle holder or by hand. This is a desired operating room and surgical procedure technique, as it reduces the amount of time between extracting the suture from the label to its actual use as a suture. Still further, in most operations and surgical procedures, the materials used for the operation or surgical procedure are counted subsequent to the operation or surgical procedure. The card or cards of the present invention provide a readily identifiable and countable material. Finally, the size of the needle and the type of suture strand can be printed on the card. This provides ready identification in a surgical procedure where more than one size and type of suture is used. The possibility of a mix-up in the sizes and types is also reduced because the suture is dispensed from the card.

SUMMARY OF THE INVENTION

The surgical suture card of this invention consists of an upper panel and a series of lower panels. The upper panel contains a series of needle retention slits near the top of the panel. The needle retention slits can be staggered, as shown in FIG. 4. In another preferred embodiment, and in place of the needle retention slits, near the top of the upper panel is a layer of foam. The foam can be of any sterilizable material, e.g., polyethylene or polypropylene. The needles are placed in the foam.

Near the middle of the upper panel are a series of suture retention slits equal in number and parallel to the needle retention slits. The suture retention slits accommodate the end of the suture. Alternatively, the suture retention slits hold the loops in double backstringing. Near the bottom of the upper panel is a series of suture loading openings equal in number and parallel to the needle retention slits. Parallel to the top of the upper panel and along the diameter of the suture openings is a score line. Extending equidistant from the top and bottom of the suture loading openings are suture retaining holes. Slits initiate from the suture loading openings and terminate in the suture retaining holes.

A series of lower panels are separated from each other and from the upper panel by parallel score lines. The lower panels are identical in size and configuration to each other. In the preferred embodiment three lower panels are used. A series of suture loading openings, similar to the suture loading openings in the upper panel, are located near the middle of the lower panels. They are equal in number and parallel to the needle retention slits in the upper panel. A score line is located along the diameter of the openings and parallel to the tops of the lower panels. As in the upper panel, a series of suture retaining holes are located near the top and bottom of the suture loading openings and a series of slits initiate from the openings and terminate in the suture retaining holes. The needle end of the surgical suture is contained in the needle retention slit. The suture strands are then loaded onto the card through the suture loading opening and pass through the slits into the suture retaining holes. The configuration of the card and the process of loading, as shown completed in FIG. 6, enables the suture to be held independently of each other suture on the card. As a result, when the needle end of the individually loaded suture is pulled from the card, it is independently dispensed without tangling or interrupting the remaining sutures or the card.

The needle ends of the surgical sutures may be single-armed or double-armed. When the suture is double-armed, two needles will be contained in one needle retention slit or placed on the layer of foam with one needle on top of the other needle.

When the suture strand is longer than the card, the extra length is placed in the suture retention slit in the upper panel and the suture strand is loaded through the suture loading openings, pass through the slits, and are held in the suture retaining holes. This is known as doublebackstringing. For the practice of this invention, any process which will enable a suture strand longer than the card to be attached to the suture retention slits through doublebackstringing can be used. The preferred configuration is graphically described in FIG. 6.

It is also to be understood that the suture retention slits could be located at other positions on the card.

In another preferred embodiment the surgical suture card described above can be folded. The score lines along the diameter of the suture loading openings are folded outward. The score lines separating the lower panels from each other and from the upper panels are folded inward. Because the lower panels are of equal size, an accordion type fold results. The card can be completely folded such that the bottom portion of the upper panel below the suture loading openings and the lower panels are folded under the remainder of the upper panel.

Any size, length or number of suture needles and any size and length of suture strands that can be used with the card in the flat configuration can be used with the card in the accordion folded position. For example, the needle ends of the sutures can be double-armed, and the suture strands can be contained in the suture retention slits through doublebackstringing. The card in the accordion fold position containing the sutures is then extended at the point of use and the sutures dispensed.

After the sutures are loaded onto the suture card, it is enclosed in a suture sleeve. The suture sleeve comprises at least two needle side flaps. In the preferred embodiment, the attachment means of the side flaps is with a slot and a tab. A needle protection flap is folded inside the side flaps. The suture sleeve and the suture card is a paper, paperboard or plastic material of sterilizable stock, which is of sufficient thickness to give adequate rigidity prior to use. The length of the needle side flaps along the side of the card is not critical to the practice of this invention. Generally, the needle side flaps will be shorter than the length of the upper panel of the card. When the side flaps are opened and laid flat and the needle protection flap is lifted and laid flat, the needle ends of the sutures are exposed for dispensing.

A suture sleeve for the surgical suture card in the accordion folded position is also within the scope of this invention. In a preferred embodiment the suture sleeve comprises two needle side flaps the length of the upper panel and a needle protection flap folded inside the needle side flaps.

Finally, a suture package comprising the suture sleeves described above is within the scope of this invention. The suture package comprises a suture sleeve and a suture card described above contained in a strippable outer pouch. The strippable outer pouch can be made of heat sealable polyethylene.

DESCRIPTION OF THE INVENTION

Figure 1:
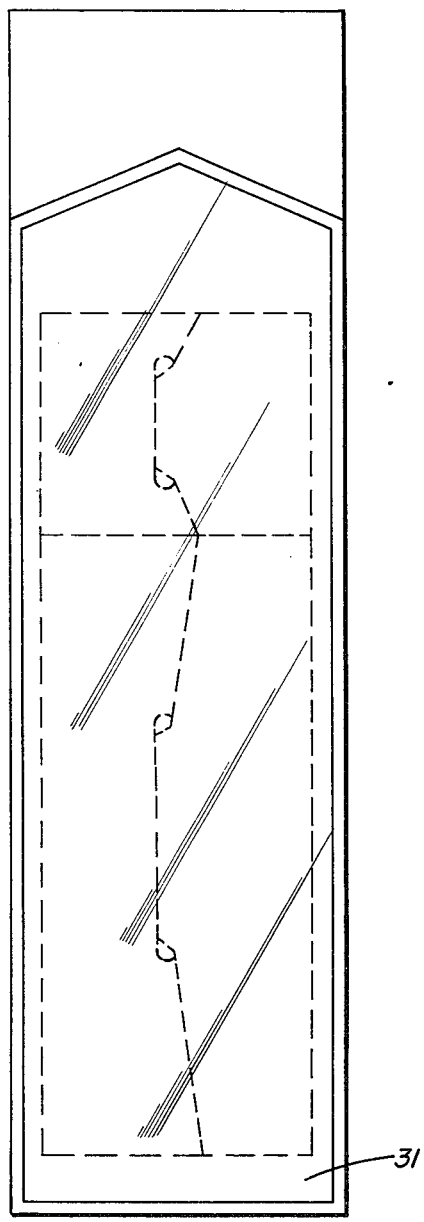
FIG. 1 shows a strippable outer envelope containing the paperboard sleeve.

The paper card may be packed in extended form or folded to fit a smaller sleeve. The complete package can provide a multiple of sutures from one package, at the point of use. The package further reduces handling by allowing each suture to be grasped directly by the needle holder and dispensed independently of the others without tangling. Product identification at the point of use.

After the sutures are loaded on the inner card it can be packed in its extended form or refolded at scores to fit a smaller sleeve. It would then be extended at the point of use and the sutures dispensed from under a sterile towel. The inner card and the sleeve can be made of paper, paperboard or plastic. A foam could also be used on the top of the inner card to hold the needles in a more orderly manner for faster assembly in manufacture and to assist in grasping the needles with the needle holder.

The inner card will reduce handling and increase efficiency in the manufacturing process. The complete package can be usefully applied to any surgical procedure requiring a multiple of the same suture or a predetermined assortment of different sutures. The package also provides a minimum of package and suture handling.

The package consists of a strippable pouch which when stripped exposes a sterile self-contained paperboard sleeve. The sleeve encloses one or more paper cards, each having a multiple of sutures affixed. The paperboard sleeve can be removed from the pouch aseptically and opened at one end to expose a paper card containing a product description label and the dispensing end of all the contained sutures. The paper card to which the sutures are affixed contain a number of cuts, slits and holes. When the suture is pulled from the dispensing end of the paper card, the suture is released without catching on any package component or other suture. The slits and holes are so dimensioned as to allow doublebackstringing of longer sutures and allow sutures to be grasped directly by the needle holder and dispensed independently of the others without tangling. Product identification is so oriented as to provide bold identification at the point of use.

The slits and holes are so dimensioned that as the card is folded in an accordion manner, the slits and small holes are directly on top of one another. In loading the sutures on the card the sutures are drawn through the slits and trapped in the holes. After all sutures are loaded in this manner, the card can be extended to full length and placed in its extended form into the paperboard sleeve. The cuts at the top of the inner card are so designed to hold the suture ends, or needles in an orderly manner for ease of grasping and to allow free suture release during dispensing.

The cuts for suture loops are so designed and positioned as to allow doublebackstringing of sutures which are longer than the card, and to allow free releasing when the suture is pulled from the dispensing end.

Sutures which may be placed on the card are: double-armed sutures of various lengths; single-armed sutures of various lengths; and non-needle sutures of various lengths; or a combination of any of the above. It should be noted that the figures depict curved needles. However straight needles could also be included as a proper suture for this package.

FIG. 1 discloses a strippable pouch 31.

Figure 2:
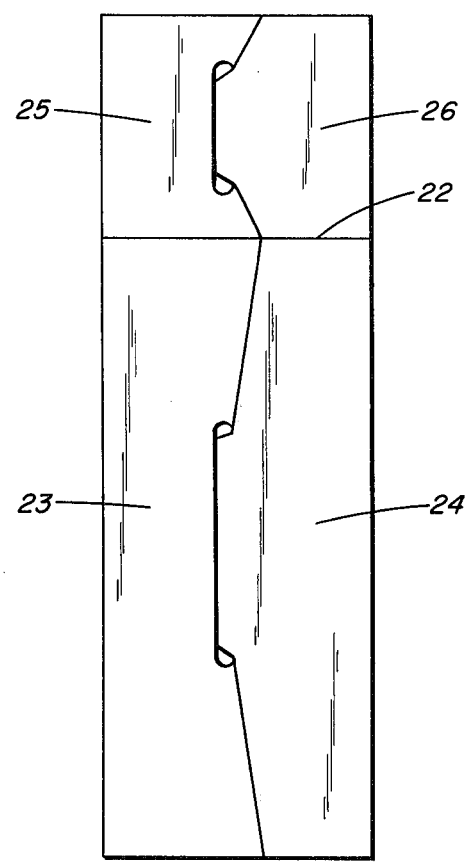
FIG. 2 shows the strand cover and needle cover side flaps of the sleeve.

FIG. 2 shows the self-contained paperboard sleeve after the strippable pouch has been removed. The needle cover side flap with tab 26 and the needle cover side flap with slot 25 are critical to the practice of this invention. The needle cover side flaps are separated from the suture cover side flaps 23 and 24 by a cut 22 along the front of the sleeve.

Figure 3:
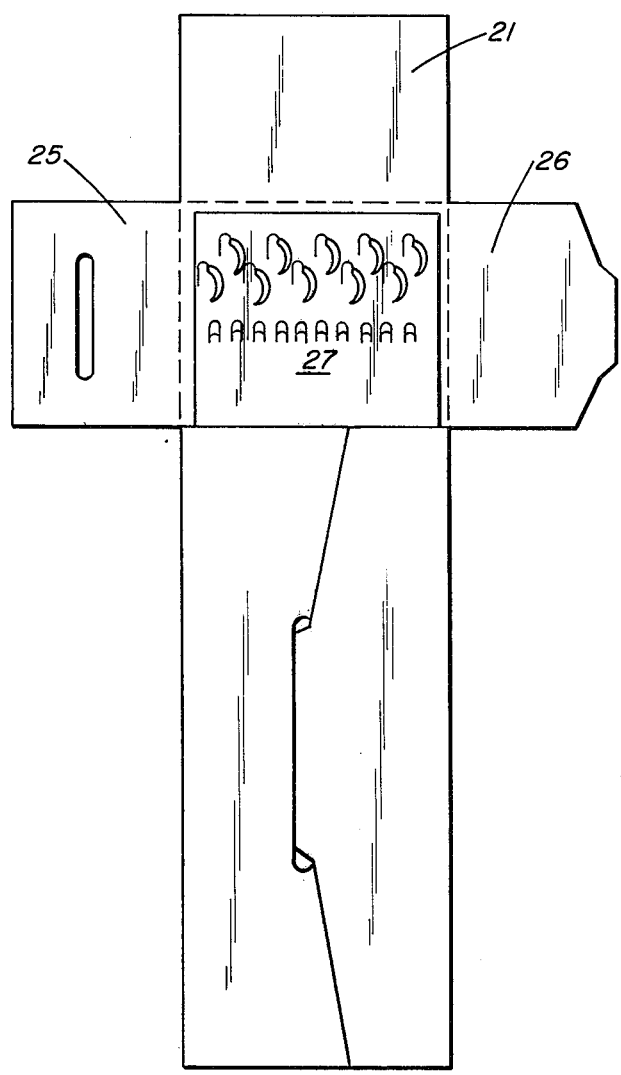
FIG. 3 shows the sleeve in position for use.

FIG. 3 shows the needle cover side flaps 25 and 26 and the needle protection flap 21 fully opened exposing the card 27. A product description label 16 is placed on the inside of the needle protection flap.

Figure 4:
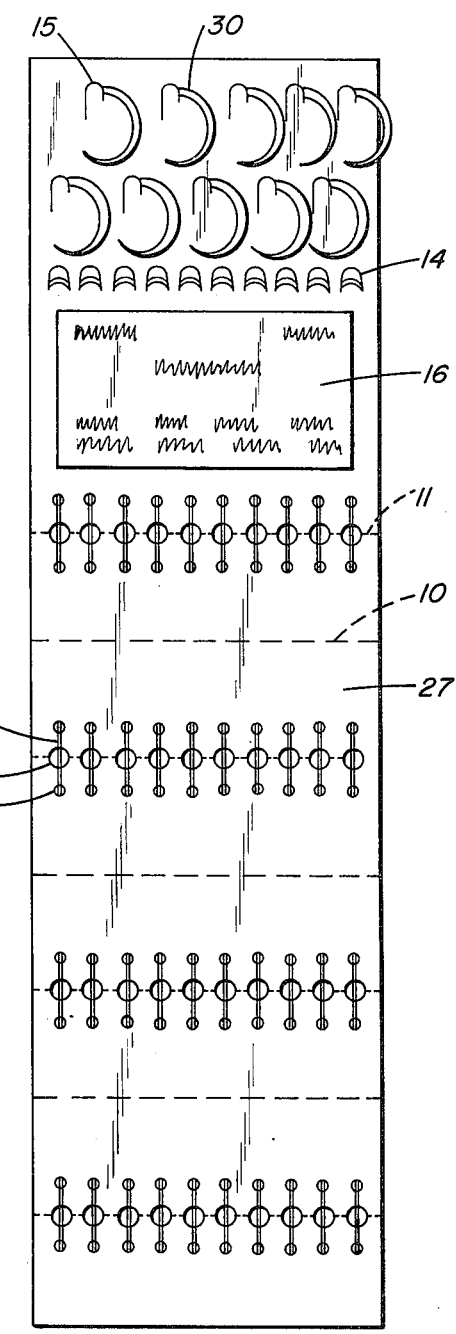
FIG. 4 shows the paper card containing double-armed sutures.

FIG. 4 describes the card 27 of FIG. 3 removed from the sleeve. Score lines 10 and 11 assist in the loading of the sutures onto the card and allow the card to be folded. Suture loading holes 12, and suture retaining holes 13 hold the suture 29 onto the card. Suture retaining slits 14 are designed to allow double-backstringing of the sutures which are longer than the card. The suture retaining slits also assist in positioning the suture for free release when the suture is pulled from the dispensing end. Needle retention slits 15 hold the needles 30 in position. Alternatively, foam could be used to hold the needles in position. Although double-armed needles are shown, it is to be understood that single-armed could also be used in the practice of this invention. When single-armed sutures are use, only one needle is placed in each needle retention slit. The candy cane design of the needle retention slit 15 assists in the loading of the needle onto the card and also aid in holding the needles in place prior to use. A product description label 16 is placed on the front side of the card. This allows positive identification of the suture.

Figure 6:
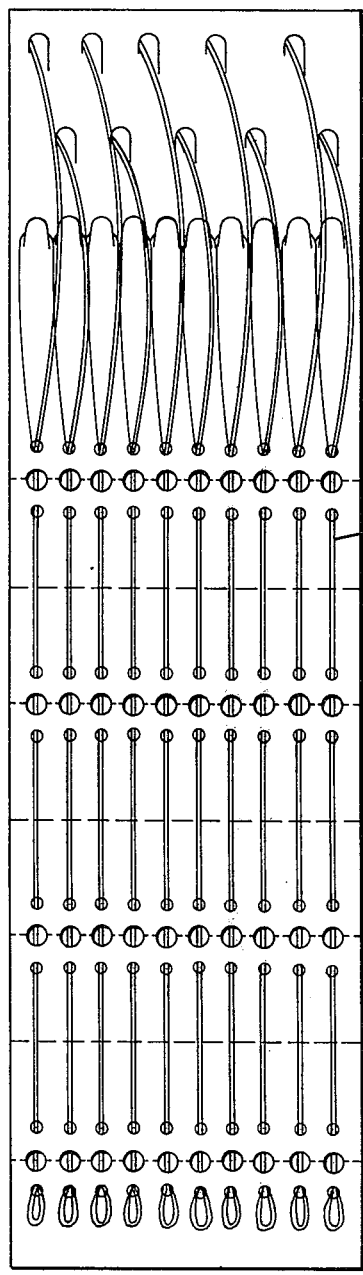
FIG. 6 is a rear view of FIG. 4.

FIG. 6 is a rear view of FIG. 4 and shows the position of the suture 29 with doublebackstringing.

Figure 5:
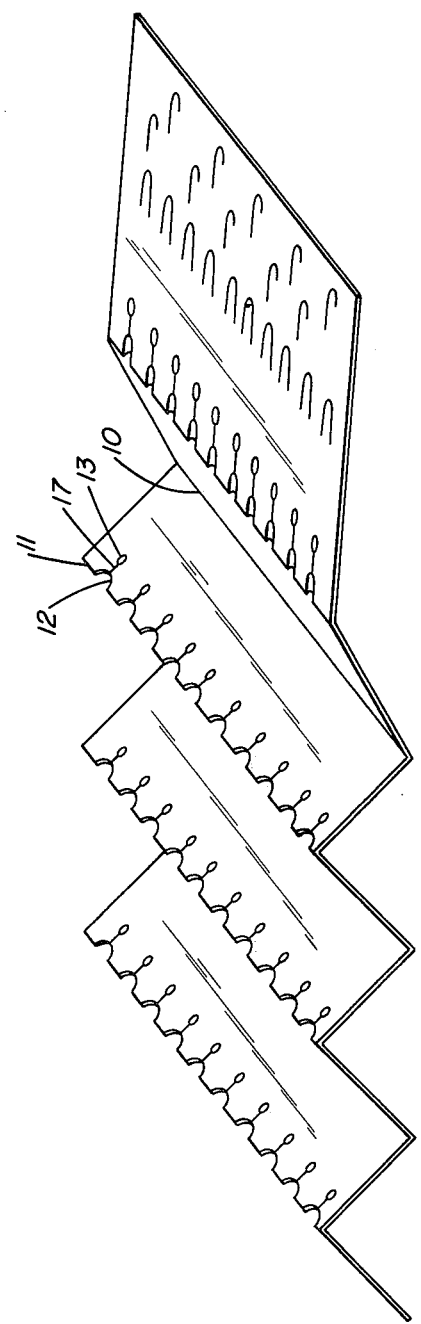
FIG. 5 is a projected view of the paper card showing the accordion folds.

FIG. 5 shows the accordion folds of the card along the score lines 10 and 11. It should be noted that the suture loading hole 12 of FIG. 4 becomes an opening as the score lines 11 are joined. When the score lines are joined, the suture is placed in the suture loading opening 12, passed through the slit 17 onto the suture retaining holes 13. The card can then be fully extended and inserted into the sleeve.

Figure 7:
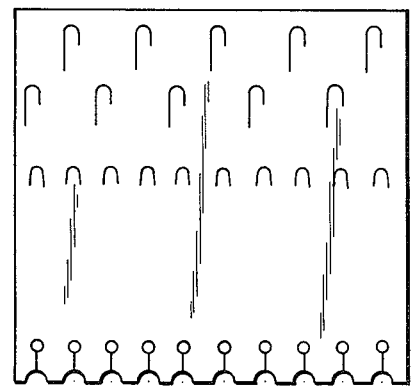
FIG. 7 shows the fully folded paper card of FIG. 5.

FIG. 7 discloses the complete accordion fold of FIG. 5 along the score lines 10 and 11. The configuration of FIG. 7 is another preferred embodiment of this invention. For example, the card of FIG. 7 could be loaded as described in FIG. 5, fully extended as shown in FIG. 4, and then refolded along the score lines which allows a more compact packaging format.

Figure 8:
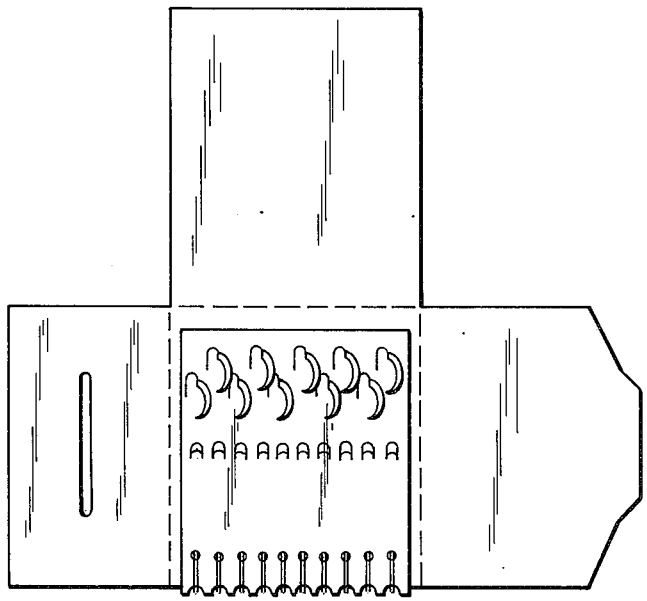
FIG. 8 shows the card of FIG. 7 containing double-armed sutures in an accommodating sleeve.

FIG. 8 shows the fully loaded card of FIG. 7 inserted into a sleeve. The card would then be extended at the point of use and the sutures dispensed.

A bottom flap 28 on the suture sleeve is optional to the practice of this invention. If used, the bottom flap is folded inside the needle cover side flaps 25 and 26.

I claim:

1. A surgical suture card consisting of an upper panel having a series of needle retention slits or a layer of foam near the top of said panel; a series of suture retention slits near the middle of said panel and a series of suture loading openings near the bottom of said panel, equal in number and parallel to said needle slits; a score line along the diameter of said openings and parallel to the top of said panel; a series of suture retaining holes adjacent the top and bottom of said openings; and a series of slits initiating from said openings and terminating in said holes, a series of lower panels having parallel score lines separating each panel and said upper panel; a series of suture loading openings near the middle of said lower panels equal in number and parallel to said needle slits; a series of score lines along the diameter of said openings and parallel to the tops of said lower panels; a series of suture retaining holes adjacent the top and bottom of said openings; and a series of slits initiating from said openings and terminating in said holes, whereby when the needle ends of surgical sutures are contained in said needle slits or placed on said layer of foam, and the suture strands are loaded onto said card through said openings and are contained in said holes, the needle end of an individual suture is independently dispensed from said card.

2. A surgical suture card described in claim 1 wherein the needle ends of said sutures are single-armed.

3. A surgical suture card described in claim 1 wherein the needle ends of said sutures are double-armed.

4. A surgical suture card described in claim 3 wherein the suture strands are loaded onto said card through said openings and are contained in said holes and said suture retention slits through doublebackstringing.

5. A suture sleeve comprising two needle side flaps having a slot and a tab, a needle protection flap folded inside said side flaps and enclosed therein a surgical suture card described in claim 1, said upper panel of said card is adjacent said side flaps of said sleeve, such that when said side flaps are opened and said protection flap is lifted, the needle ends of said sutures are exposed.

6. A suture sleeve comprising two needle side flaps having a slot and a tab, a needle protection flap folded inside said side flaps and enclosed therein a surgical suture card described in claim 1 wherein said score lines along the diameter of said openings are folded outward, and said score lines separating said lower panels and said upper panel are folded inward such that the bottom portion of said upper panel and said lower panels are folded under the remainder of said upper panel and the top portion of said upper panel is adjacent said needle flap of said sleeve, such that when said side flaps are opened and said needle flap is lifted, the needle ends of said sutures are exposed.

7. A suture package comprising a strippable outer pouch containing a suture sleeve described in claim 5.

8. A suture package comprising a strippable outer pouch containing a suture sleeve described in claim 6.

* * * * *